United States Patent [19]
Ting

[11] Patent Number: 5,192,316
[45] Date of Patent: Mar. 9, 1993

[54] OCULAR DEVICE

[75] Inventor: Albert C. Ting, Laguna Niguel, Calif.

[73] Assignee: Allergan, Inc., Irvine, Calif.

[21] Appl. No.: 898,241

[22] Filed: Jun. 12, 1992

Related U.S. Application Data

[63] Continuation of Ser. No. 443,102, Nov. 28, 1989, abandoned, which is a continuation of Ser. No. 156,033, Feb. 16, 1988, abandoned.

[51] Int. Cl.$^5$ .............................................. A61F 2/14
[52] U.S. Cl. ........................................ 623/5; 623/11
[58] Field of Search ................................ 623/4–6; 351/160 R; 128/305, 303.1; 604/893, 895

[56] References Cited

U.S. PATENT DOCUMENTS

| | | | |
|---|---|---|---|
| 2,714,721 | 8/1955 | Stone | 623/5 |
| 3,986,510 | 10/1976 | Higuchi | 424/428 |
| 4,346,482 | 8/1982 | Tennant | 128/305 |
| 4,452,925 | 6/1984 | Kuzma et al. | |
| 4,642,118 | 2/1987 | Kuroyanagi et al. | |
| 4,676,790 | 6/1987 | Kern | 623/5 |
| 4,713,244 | 12/1987 | Bawa | 351/160 R |
| 4,715,858 | 12/1987 | Lindstrom | 128/305 |
| 4,740,498 | 4/1988 | Hirao et al. | 530/386 |
| 4,828,563 | 5/1989 | Müller-Lierheim | 623/16 |
| 4,919,659 | 4/1990 | Horbett et al. | 427/2 X |
| 4,979,959 | 12/1990 | Guire | 623/11 X |
| 4,983,181 | 1/1991 | Civerchia | 623/5 |

FOREIGN PATENT DOCUMENTS

| | | |
|---|---|---|
| 0206025 | 12/1986 | European Pat. Off. |
| 0224460 | 6/1987 | European Pat. Off. |
| 2178963A | 2/1987 | United Kingdom |
| 8802622 | 4/1988 | World Int. Prop. O. |
| 8904153 | 5/1989 | World Int. Prop. O. ............ 623/11 |
| 9000887 | 2/1990 | World Int. Prop. O. ............ 623/11 |

Primary Examiner—Randall L. Green
Assistant Examiner—D. Willse
Attorney, Agent, or Firm—Frank J. Uxa, Jr.

[57] ABSTRACT

An ocular device comprising a lens structure capable of being surgically associated with a living cornea to change the optical properties of the eye associated with the living cornea and an effective amount of at least one added component associated with the lens structure and acting to promote at least one of the growth of epithelial cells of the cornea onto the lens structure and the adhesion of the living cornea to the lens structure.

20 Claims, 1 Drawing Sheet

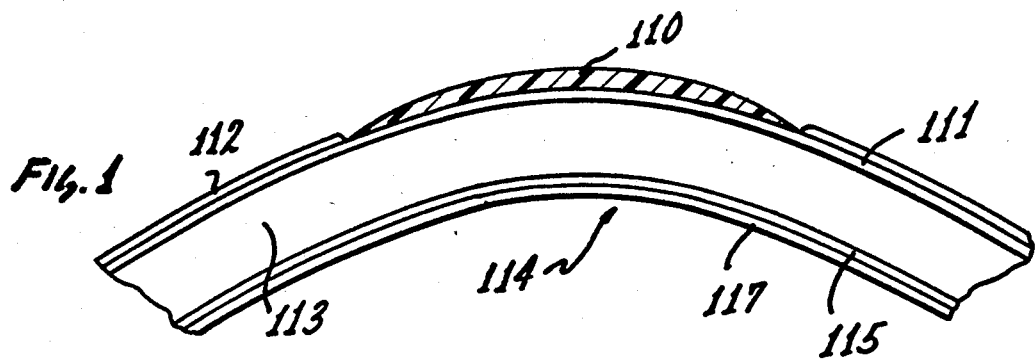
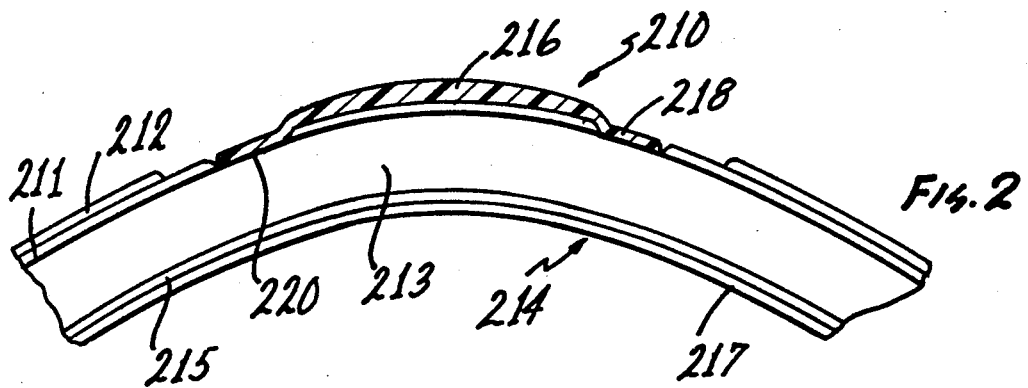
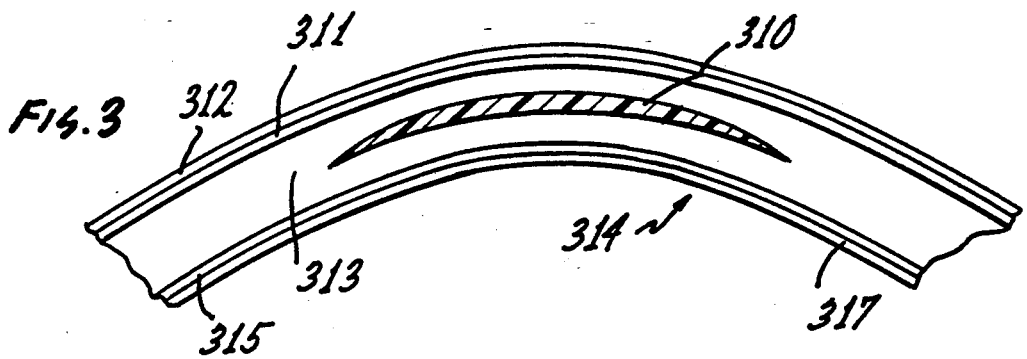
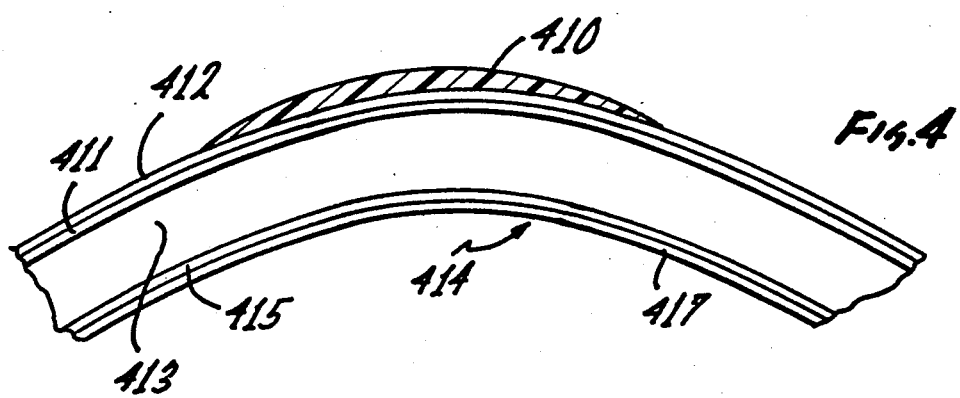

OCULAR DEVICE

This application is a continuation of application Ser. No. 443,102, filed Nov. 28, 1989, now abandoned, which, in turn, is a continuation of application Ser. No. 156,033, filed Feb. 16, 1988 now abandoned.

BACKGROUND OF THE INVENTION

This invention relates to an ocular device which can be surgically associated with, e.g., surgically implanted into, a living cornea or, in another embodiment, is suitable for being located in proximity to a damaged, living cornea. More particularly, the invention relates to such ocular devices which promote at least one of the growth and adhesion of the living cornea, e.g., corneal epithelium, onto the ocular device after surgery and act to correct a vision problem or, which promote the healing of the damaged cornea and may act to correct a vision problem, e.g., a refractive error.

The cornea comprises five layers, including an outer layer of epithelial cells, Bowman's membrane immediately posterior of the cells, the stroma immediately posterior of Bowman's membrane, Descemet's membrane immediately posterior of the stroma and the endothelium immediately posterior of Descemet's membrane. A number of surgical operations involve implanting a corrective lens structure into or onto one or more of these corneal components. For example, in one form of eye surgery, the layer of epithelial cells is removed and a corrective lens structure is placed and secured at the location where the cells were removed. In another form of eye surgery, a portion of the layer of epithelial cells is removed and then a wedge-shaped annulus from Bowman's membrane and the underlying stroma is removed. An incision is then made from the posterior end of the resulting groove radially outwardly in an annular zone to define a flap. A corrective lens structure is attached by inserting the wing of the lens structure beneath the corneal flap and fixing, e.g., suturing, it in place. In addition, a corrective lens structure can be placed entirely within the stroma. This surgical procedure involves making an incision in the cornea to gain access to the stroma and also involves disrupting the stroma by placing a lens structure therein.

In each of these surgical procedures, it is highly desirable, even necessary, for the long term viability of such lens onlays or implants that the cornea, e.g., the epithelial cells, grow onto the lens structure and/or adhere to the lens structure. Achieving such growth and adhesion has been one substantial problem inhibiting the use of such corneal onlay and implant procedures.

One suggestion to overcome this problem has been to add drops of liquid fibronectin solution to the cornea after surgery to enhance the growth of the epithelial cells. However, this approach has not proven to be totally successful. For example, the drops must be added to the eye very frequently. This is troublesome and may lead to discomfort. Even with the frequent addition of drops, it is very difficult to have an effective amount of the fibronectin present. The natural cleansing action, e.g., tearing action, of the eye tends to eliminate the fibronectin.

Another situation which often occurs is that the cornea becomes damaged, e.g., in sports-related incidents and other accidents. Since such damage may cause relatively great discomfort and/or adversely affect one's vision, it is very desirable to heal the damage as soon as possible.

SUMMARY OF THE INVENTION

The present invention provides an ocular device which effectively promotes the growth and/or adhesion of a living cornea to a lens structure and/or the healing of a damaged, living cornea. Thus, by employing the present devices, more rapid and successful recuperation from eye surgery or corneal damage is achieved. Moreover, these beneficial results are obtained with little or no additional effort, care or treatment, e.g., on the part of the patient. For example, no drops or other additive materials are repeatedly added to the eyes.

In one embodiment, the present ocular device comprises a lens means or structure capable of being surgically associated with, preferably attached to, a living cornea, and an effective amount of at least one added component associated with the lens structure and acting to promote at least one of the growth of epithelial cells of the cornea onto the lens structure and the adhesion of the living cornea to the lens structure. The lens means, when surgically associated with, e.g., surgically implanted into or onto, the living cornea, acts to change the optical properties, e.g., correct vision deficiencies, of the eye associated with the living cornea.

By "promoting at least one of the growth of epithelial cells onto the lens structure and the adhesion of the living cornea to the lens structure" is meant that the present added component is effective to encourage and/or facilitate at least one of the growth of the epithelial cells over the lens structure, which is often synthetic in nature, and the adhesion of corneal cells, e.g., newly formed epithelial cells, to the lens structure. Both such growth and adhesion are highly desirable in order to achieve successful corneal implant and onlay surgeries.

The lens structure is preferably surgically attached, e.g., sutured and the like, to the living cornea, and the added component is effective to promote the adhesion of the living cornea to the lens structure. After such adhesion, the corneal cells themselves act to hold the lens structure in place, for example, after the sutures are removed or dissolve.

The added component may be associated with, e.g., attached or secured to, deposited on and the like, the lens structure at or near the external surface of the lens structure. However, it is preferred that the added component be located within the lens structure, more preferably substantially uniformly within the lens structure. In one embodiment in which the ocular device is adapted to be surgically associated with the cornea, e.g., surgically implanted into the cornea, the added component is preferably substantially non-degradable and non-leachable or non-extractable from the lens structure at the conditions of use, i.e., in the patient's eye. In one particularly useful embodiment, the added component is chemically bonded, especially covalently bonded, to the lens structure. Such covalent bonding acts to hold the added component in association with the lens structure and to minimize the amount of added component that is lost during use.

In another embodiment, the present invention involves an ocular device comprising a lens means or structure capable of being placed in proximity, e.g., substantially directly on, a damaged, living cornea, and at least one added component associated with, e.g., secured or attached to, deposited on, combined with and the like, the lens structure. This added component is capable of being released from the association with the lens structure over a period of time, preferably at least about 12 hours, more preferably in the range of about 2 days to about 20 days or more, to promote healing of the damaged, living cornea. In this embodiment, the present ocular device may be considered a contact lens which is placed substantially directly on the cornea. This approach to providing the added component to a damaged, living cornea is far superior to repeatedly adding drops of material to the eye. For example, the release of the added component from the lens structure can be more effectively controlled so that a useful amount of the added component is substantially continuously present to promote the healing of the cornea. Also, it is not necessary to repeatedly and continuously add drops to the damaged eye, a procedure which is often troublesome and may cause discomfort.

In this embodiment, the added component may be located at or near the external surface of the lens structure. In order to provide a more uniform time release of the added component, it is preferred that the added component be located within the lens structure. Preferably, the added component is physically associated with, i.e., not chemically bonded to, the lens structure in the "contact lens" embodiment of the present invention. It is important that the added component be released from the lens structure over a period of time. As noted above, chemical bonding, e.g., covalent bonding, of the added component to the lens structure often acts to substantially eliminate this release, which release, in the "contact lens" embodiment of the present invention, has been found to be very useful.

The lens structure in the "contact lens" embodiment may or may not be structured to change the optical properties, e.g., correct vision deficiencies, of the eye associated with the damaged, living cornea. One primary function of the lens structure in this embodiment is to provide a substrate for the useful time release of the added component. Another useful function of the lens structure is to provide protection for the damaged, living cornea.

Any suitable added component may be utilized in the present invention provided that it functions as described herein and has no substantial or unacceptable adverse effect on the eye or the patient being treated. By "added component" is meant a component or components which function as described herein and which have not heretofore been included in or with lens structures as described herein. Among the added components useful in the present invention are various growth factors and adhesion factors, which promote the growth and adhesion, respectively, of the corneal cells as described herein. In one embodiment, the added component is a protein. Useful added components include those selected from the group consisting of fibronectin, collagen, cell attachment proteins, anti-gelatin factor, cold-insoluble globulin, chondronectin, laminin, epidermal growth factor (EGF), mussel adhesive protein, derivatives of each of the above and mixtures thereof. Fibronectin, derivatives of fibronectin, EGF, derivatives of EGF and mixtures thereof are especially useful.

The lens means or structure can be fabricated from any suitable material or materials of construction, provided that the so constructed lens structure functions as described herein and has no substantial adverse or detrimental effect- on the eye or the patient being treated. The lens structure should be water permeable and nutrient permeable so that the lens structure does not unduly restrict the flow of nutrients to the corneal epithelium. Although the lens structure may be made of a naturally occurring material, it is preferred to use synthetic materials, more preferably synthetic polymeric materials. In addition, both physical and chemical blends or combinations of natural materials and synthetic materials may be used in the present lens structures. A great many polymeric materials have been suggested for use in lens structures. Synthetic polymeric materials which are useful in the present invention include homopolymers and copolymers derived from mono- and diolefins, mixtures of such polymers, polystyrene, copolymers of styrene and of α-methylstyrene, graft copolymers of styrene, halogen-containing vinyl polymers, polymers derived from α, β-unsaturated acids and derivatives thereof, polymers derived from unsaturated alcohols and amines, homopolymers and copolymers derived from epoxides, polyacetals, polyalkylene oxides, polyphenylene oxides, polyurethanes and polyureas, polycarbonates, polysulfones, polyamides and copolyamides, polyesters, cross-linked polymers which are derived from aldehydes plus phenols, ureas or melamine, alkyd resins, unsaturated polyester resins, silicones, hydrogel-forming polymers and the like.

The lens structure of the present ocular device is preferably made of polymers derived from α, β-unsaturated acids and derivatives thereof, polyurethanes, silicones and hydrogel-forming polymers. Hydrogel-forming polymers are especially useful because of their outstanding permeability characteristics.

In order to covalently bond the added component onto the lens structure, it may be necessary to derivatize either one or both of the added component and the lens structure. The derivative or derivatives employed depend, for example, on the specific lens structure material used and on the specific added component used. In one particularly useful embodiment, one of the lens structure material or added component is reacted with a difunctional component. One of the functional groups of the difunctional component reacts with, and is covalently bonded to, the lens structure material or the added component and the other functional group is available to be covalently bonded to the other of the lens structure material or the added component.

Any suitable difunctional component may be employed provided that it has the ability to covalently bond to both the specific lens structure material and added component being used. Of course, the difunctional component should have no substantial adverse effect on the ocular device or on its use. Examples of difunctional components which may be employed with certain lens structure materials and added components include aldehydes, such as glutaraldehyde and the like, and imides such as carbodiimide.

The difunctional component may be reacted with the lens structure material and added component in separate reaction steps or in a single reaction step with all reactants present.

In another embodiment, the covalent bonding of the lens structure material and added component may be promoted or induced by exposing these materials and components to radiation, e.g., gamma radiation, or to a plasma treatment.

These and other aspects and advantages of the present invention are set forth in the following detailed description and claims, particularly when considered in conjunction with the accompanying drawings in which like parts bear like reference numerals.

BRIEF DESCRIPTION OF THE DRAWINGS

FIG. 1 is an enlarged axial, cross-sectional view showing an ocular device according to the present invention attached to a cornea.

FIG. 2 is an enlarged axial, cross-sectional view showing another ocular device according to the present invention attached to a cornea.

FIG. 3 is an enlarged axial, cross-sectional view showing an ocular device according to the present invention inserted in the stroma of a cornea.

FIG. 4 is an enlarged axial, cross-sectional view showing an ocular, device according to the present invention in contact with a cornea.

DETAILED DESCRIPTION OF THE DRAWINGS

Referring now to FIG. 1, an ocular device in the form of a corneal onlay, shown generally at 110, is situated on and attached (sutured) to the Bowman's membrane 111 of a living cornea 114. Also included in cornea 114 is epithelial cell layer 112, stroma 113, Descemet's membrane 115 and the endothelium 117. Corneal onlay 110, which is structured to correct one or more vision problems caused by defects in cornea 114 or in one or more other components of the eye, is set in place by surgically stripping or abrading away a desired area of the epithelial cell layer 112, placing corneal onlay 110 on this stripped area and securing corneal onlay 110 in place by suturing it to Bowman's membrane 111. The onlay 110 is placed with respect to the cornea 114 as shown in FIG. 1, so that the corneal onlay 110 is coaxial with the optical axis of the eye.

Once this surgical procedure is accomplished, epithelial cell layer 112 is to grow onto and attach or adhere to corneal onlay 110.

Corneal onlay 110 is made of a water permeable, optically clear polymer material, such as poly(hydroxyethyl) methacrylate, which is biocompatible and suitable for use in corneal onlays. Fibronectin, or a derivative of fibronectin, is covalently bonded to the polymeric material of corneal onlay 110. This fibronectin or fibronectin derivative is substantially uniformly distributed in the polymeric material and accounts for about 1% by weight of the corneal onlay 110.

After the corneal onlay 110 is attached to Bowman's membrane 111, the fibronectin or derivative thereof in corneal onlay 110 acts to promote the growth of epithelial cell layer 112 onto corneal onlay 110 and the adhesion of epithelial cell layer 112 to corneal onlay 110. Ultimately, layer 112 completely overgrows corneal onlay 110 and is securely attached to corneal onlay 110. The rate at which this occurs is substantially faster when utilizing corneal onlay 110 relative to an onlay which contains no fibronectin or comparable substance.

Of course, it is understood that the fibronectin or derivative thereof covalently bonded in corneal onlay 110 can be replaced, in whole or in part, by one or more other added components effective to promote the growth of epithelial cell layer 112 onto corneal onlay 110 and/or adhesion or attachment of epithelial cell layer 112 to corneal onlay 110.

Referring now to FIG. 2, an ocular device in the form of an alternate corneal onlay or epikeratophakia lenticule, shown generally at 210, is situated on and attached (sutured) to the Bowman's membrane 211 of a living cornea 214. Each element of cornea 214 in FIG. 2 which is also shown as an element of cornea 114 in FIG. 1 has a reference numeral increased by 100 relative to the same element shown in FIG. 1. Corneal onlay 210 comprises a circular optic 216 and a annular wing 218 surrounding the optic. The onlay 210 is placed with respect to the cornea 214 as shown in FIG. 2, with the optic 216 being coaxial with the optical axis of the eye and with the annular wing 218 being received in an annular abraded zone 220. This zone 220 is obtained by stripping and/or abrading a portion of the epithelial cell layer 212 and the Bowman's membrane 211. A useful apparatus and procedure for performing this stripping-/abrading are described in commonly assigned U.S. patent application Ser. No. 102,344, filed Sep. 29, 1987, now U.S. Pat. No. 4,834,748 which is incorporated in its entirety herein by reference.

Corneal onlay 210, and in particular optic 216, is structured to correct one or more problems caused by defects in cornea 214 or in one or more other components of the eye.

Once the surgical procedure of securing corneal onlay 210 in place as shown in FIG. 2 is accomplished, epithelial cell layer 212 is to grow onto corneal onlay 210 and attach or adhere to corneal onlay 210.

Corneal onlay 210 is made of substantially the same material as is corneal onlay 110.

After corneal onlay 210 is attached to cornea 214 as shown in FIG. 2, the fibronectin or derivative thereof in corneal onlay 210 acts to promote the growth of epithelial cell layer 212 onto corneal onlay 210 and adhesion of epithelial cell layer 212 onto corneal onlay 210. Ultimately, layer 212 completely overgrows corneal onlay 210 and is, securely attached to corneal onlay 210. The rate at which this occurs is substantially faster when utilizing corneal onlay 210 relative to an onlay which contains no fibronectin or comparable substance.

As with corneal onlay 110, other added components effective to promote the growth of epithelial cell layer 212 onto corneal onlay 210 and/or adhesion or attachment of epithelial cell layer 212 to corneal onlay 210 can be used in corneal onlay 210 all or a part of the fibronectin or derivative thereof.

Referring now to FIG. 3, an ocular device in the form of an intrastromal lens, shown generally at 310, is situated in the stroma 313 of living cornea 314. Each element of cornea 314 in FIG. 3 which is also shown as an element of cornea 114 in FIG. 1 has a reference numeral increased by 200 relative to the same element shown in FIG. 1. The lens 310 is coaxial with the optical axis of the eye and is placed and secured in the stroma 313 using conventional surgical procedures. Lens 310 is structured to correct one or more vision problems caused by defects in cornea 314 or in one or more other components of the eye.

Lens 310 is made of substantially the same material as the corneal onlay 110.

After lens 310 is surgically implanted in stroma 313 as shown in FIG. 3, the fibronectin or derivative thereof in lens 310 acts to promote the adhesion of the tissue of the stroma 313 to lens 310. Ultimately, the stroma 313 is securely attached to lens 310. The rate at which this occurs is substantially faster when utilizing lens 310 relative to an intrastromal lens which contains no fibronectin or comparable substance.

Other added components effective to promote the adhesion or attachment to stroma 313 to lens 310 can be used in lens 313 in place, in whole or in part, of the fibronectin or derivative thereof.

Referring now to FIG. 4, an ocular device in the form of a contact lens, shown generally at 410, is situated on the epithelial cell layer 412 of a living cornea 414. A thin film of natural lubrication or moisture, not shown, may exist between contact lens 410 and layer 412.

In addition to epithelial cell layer 412, living cornea 414 also includes Bowman's membrane 411 and stroma 413 Descemet's membrane 415 and the endothelium 417.

Contact lens 410 is made of water permeable, optically clear poly(hydroxyethyl) methacrylate which is biocompatible and suitable for use in contact lens construction. Physically mixed with and substantially uniformly distributed in the polymeric material is fibronectin, which accounts for about 1% by weight of the contact lens 410. Contact lens 410 may or may not be structured to correct one or more vision problems caused by defects in the cornea 414 or in one or more other components of the eye. It is important that the fibronectin in contact lens 410 be released from contact lens 410 over a period of time to promote the healing of cornea 414.

The epithelial cell layer 412 of the cornea 414 has been accidentally damaged and healing is required. Contact lens 410 is placed in proximity to the damaged portion of layer 412. Over a period of time, fibronectin is released from contact lens 410 and promotes the needed healing of layer 412. Applying fibronectin to the damaged layer 412 in this manner provides substantial advantages relative to using drops of fibronectin-containing solution. With contact lens 410, fibronectin is supplied continuously to the layer 412, rather than intermittently as with drops. Also, the gradual release of fibronectin from contact lens 410 provides a more effectively controlled dosage of fibronectin, and therefore more effective utilization of this growth factor. If desired, the fibronectin can be micro-encapsulated within contact lens 410 to further control the timed release of the fibronectin.

Of course it is understood that the fibronectin in contact lens 410 can be replaced, in whole or in part, by one or more other added components effective to promote the healing of epithelial cell layer 412.

While this invention has been described with respect to various specific examples and embodiments, it is to be understood that the invention is not limited thereto and that it can be variously practiced within the scope of the following claims.

What is claimed is:

1. A method for correcting the optical properties of an eye comprising:
    surgically implanting into or onto a living cornea an ocular device comprising lens means effective to change the optical properties of the eye associated with said living cornea, and at least one added component covalently bonded to and substantially uniformly located throughout said lens means and acting to promote at least one of the growth of epithelial cells of said living cornea onto said lens means and the adhesion of said living cornea to said lens means.

2. The method of claim 1 wherein said surgically implanting step comprises attaching said lens means to said living cornea, and said added component acts to promote the adhesion of said living cornea to said lens means.

3. The method of claim 1 wherein said lens means comprises a synthetic polymeric material which is water permeable.

4. The method of claim 3 wherein said synthetic polymeric material is a hydrogel-forming polymer.

5. The method of claim 1 wherein said added component is selected from the group consisting of fibronectin, collagen, cell attachment proteins, anti-gelatin factor, biologically active polypeptides, cold-insoluble globulin, chondronectin, laminin, epidermal growth factor, mussel adhesive protein, derivatives thereof and mixtures thereof.

6. The method of claim 1 wherein said added component is selected from the group consisting of fibronectin, derivatives of fibronectin, epidermal growth factor, derivatives of epidermal growth factor, and mixtures thereof.

7. An ocular device comprising a lens means structured to be surgically implanted into or onto a living cornea to change the optical properties of the eye associated with said living cornea and at least one added component covalently bonded to and substantially uniformly located throughout said lens means and acting to promote at least one of the growth of epithelial cells of said living cornea onto said lens means and the adhesion of said living cornea to said lens means.

8. The ocular device of claim 7 wherein said lens means is structured to be surgically attached to said living cornea and with said added component acting to promote the adhesion of said living cornea to said lens means.

9. The ocular device of claim 7 wherein said lens means comprises a synthetic polymeric material which is water permeable.

10. The ocular device of claim 9 wherein said synthetic polymeric material is a hydrogel-forming polymer.

11. The ocular device of claim 7 wherein said added component is selected from the group consisting of fibronectin, collagen, cell attachment proteins, anti-gelatin factor, biologically active polypeptides, cold-insoluble globulin, chondronectin, laminin, epidermal growth factor, mussel adhesive protein, derivatives thereof and mixtures thereof.

12. The ocular device of claim 7 wherein said added component is selected from the group consisting of fibronectin, derivatives of fibronectin, epidermal growth factor, derivatives of epidermal growth factor, and mixtures thereof.

13. An ocular device comprising a lens means having an external surface and being structured to be surgically implanted into or onto a living cornea to change the optical properties of the eye associated with said living cornea and at least one added component covalently bonded to said lens means, at least a portion of which is located as other than a surface coating, and acting to promote at least one of the growth of epithelial cells of said living cornea onto said lens means and the adhesion of said living cornea to said lens means.

14. The ocular device of claim 13 wherein a portion of said added component is located at or near said external surface.

15. The ocular device of claim 13 wherein said lens means is structured to be surgically attached to said living cornea and with added component acting to promote the adhesion of said living cornea to said lens means.

16. The ocular device of claim 13 wherein said lens means, other than said added component, comprises a material selected from the group consisting of synthetic materials and mixtures of (a) one or more synthetic materials and (b) one or more naturally occurring materials.

17. The ocular device of claim 13 wherein said lens means comprises a synthetic polymeric material which is water permeable.

18. The ocular device of claim 17 wherein said synthetic polymeric material is a hydrogel-forming polymer.

19. The ocular device of claim 13 wherein said added component is selected from the group consisting of fibronectin, collagen, cell attachment proteins, anti-gelatin factor, biologically active polypeptides, cold-insoluble globulin, chondronectin, laminin, epidermal growth factor, mussel adhesive protein, derivatives thereof and mixtures thereof.

20. The ocular device of claim 13 wherein said added component is selected from the group consisting of collagen, derivatives thereof and mixtures thereof.

* * * * *